(12) United States Patent
Smith, Jr. et al.

(10) Patent No.: US 7,408,090 B2
(45) Date of Patent: Aug. 5, 2008

(54) METHOD OF OPERATING DOWNFLOW BOILING POINT REACTORS IN THE SELECTIVE HYDROGENATION OF ACETYLENES AND DIENES

(75) Inventors: Lawrence A. Smith, Jr., Houston, TX (US); Abraham P. Gelbein, Raleigh, NC (US)

(73) Assignee: Catalytic Distillation Technologies, Pasadena, TX (US)

( * ) Notice: Subject to any disclaimer, the term of this patent is extended or adjusted under 35 U.S.C. 154(b) by 516 days.

(21) Appl. No.: 11/101,098

(22) Filed: Apr. 7, 2005

(65) Prior Publication Data
US 2006/0229477 A1 Oct. 12, 2006

(51) Int. Cl.
C07C 5/03 (2006.01)
(52) U.S. Cl. .................... 585/259; 585/261
(58) Field of Classification Search .......... 585/259, 585/261
See application file for complete search history.

(56) References Cited

U.S. PATENT DOCUMENTS

| | | | | |
|---|---|---|---|---|
| 4,316,997 A | 2/1982 | Vaughan | .............. | 385/458 |
| 4,317,949 A | 3/1982 | Vaughan | .............. | 585/458 |
| 4,419,328 A | 12/1983 | Walsh | .............. | 422/62 |
| 4,529,573 A | 7/1985 | Varady | .............. | 422/111 |
| 4,621,062 A | 11/1986 | Stewart et al. | ........... | 436/55 |
| 4,950,803 A | 8/1990 | Smith, Jr. et al. | ......... | 568/697 |
| 5,003,124 A | 3/1991 | Smith, Jr. et al. | ......... | 585/526 |
| 5,177,289 A | 1/1993 | Smith, Jr. et al. | ......... | 585/526 |
| 5,190,730 A | 3/1993 | Smith, Jr. et al. | ......... | 422/109 |
| 5,792,428 A | 8/1998 | Bakshi et al. | ........... | 422/112 |
| 5,840,259 A | 11/1998 | Adams | .............. | 422/191 |
| 6,335,473 B1 | 1/2002 | Bakshi et al. | ........... | 568/697 |
| 6,413,413 B1 | 7/2002 | Smith, Jr. | .............. | 208/213 |
| 6,596,913 B1 | 7/2003 | Loescher | .............. | 585/504 |
| 6,620,965 B1 | 9/2003 | Adams et al. | ........... | 560/245 |
| 6,824,676 B1 | 11/2004 | Podrebarac et al. | ..... | 208/210 |
| 6,858,770 B2 | 2/2005 | Smith, Jr. et al. | ......... | 585/720 |
| 6,867,338 B2 | 3/2005 | Gelbein et al. | .......... | 585/259 |
| 2002/0022754 A1* | 2/2002 | Boyer et al. | ........... | 585/265 |
| 2003/0233017 A1 | 12/2003 | Gelbein et al. | | |
| 2005/0113612 A1 | 5/2005 | Bakshi et al. | ........... | 585/255 |

OTHER PUBLICATIONS

Mordechay Herskowitz et al, Trickle-Bed Reactors: A Review, AIChE Journal (vol. 29, No. 1) Jan. 1983.

(Continued)

*Primary Examiner*—Thuan Dinh Dang
(74) *Attorney, Agent, or Firm*—Osha Liang LLP

(57) ABSTRACT

Acetylenes and dienes in a stream containing hydrogen, methane, $C_2$-$C_6$ olefins and paraffins, $C_2$-$C_6$ acetylenes and dienes, benzene, toluene, xylenes, and other $C_6$+ components are hydrogenated in a downflow boiling point reactor wherein the heat of reaction is absorbed by the liquid in the reactor which produces a vapor. Besides the feed to the reactor there is a recirculating stream which is fed at a rate sufficient to ensure that the catalyst particles within the reactor are wetted. A third stream, which is provided from a second downstream liquid/vapor separator from partially condensed vapor from the first downstream liquid/vapor separator corresponding to the mass evaporated in the reactor, is fed to the reactor. The composition of the third stream controls the steady state composition of the liquid flowing through the reactor.

3 Claims, 1 Drawing Sheet

OTHER PUBLICATIONS

M.L. Derrien et al., The IFP Selective Hydrogenation Process, Chemical Engineering Process (vol. 70, No. 1) Jan. 1974.

International Application No. PCT/US2006/03083; International Search Report and Written Opinion, dated Aug. 10, 2007 (6 pages).

* cited by examiner

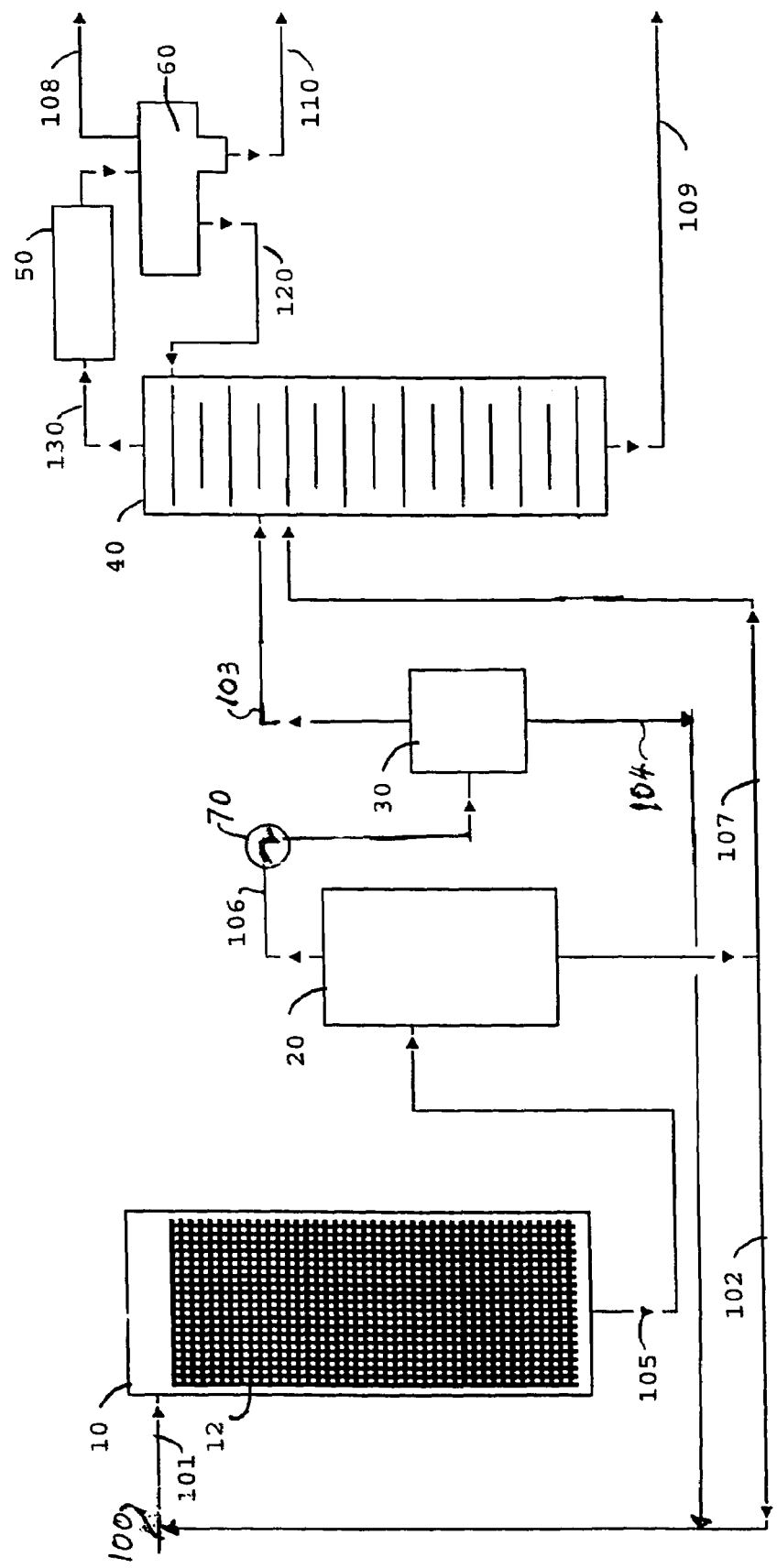

METHOD OF OPERATING DOWNFLOW BOILING POINT REACTORS IN THE SELECTIVE HYDROGENATION OF ACETYLENES AND DIENES

BACKGROUND OF THE INVENTION

1. Field of the Invention

The present invention relates to an improved process for selectively hydrogenating acetylenes and dienes in a hydrocarbon stream in a downflow boiling point reactor.

2. Related Information

The vapor product stream from the quench system of a hydrocarbon steam cracker typically consists mainly of hydrogen, methane, $C_2$-$C_6$ olefins and paraffins, $C_2$-$C_6$ acetylenes and dienes, benzene, toluene, xylenes, and other $C_6$+ components. Separation and recovery of the products according to carbon number is generally accomplished in a sequential distillation system after the first separation of hydrogen from the methane in a high pressure cold box system. The design of the distillation system is complicated by the fact that the differences in relative volatility of the olefins, acetylenes, and dienes of the same carbon number are small making it difficult to produce the pure olefin products. One method of circumventing this problem is to first separate the carbon number fractions and then to selectively hydrotreat each fraction to convert the acetylene and/or diene to its corresponding olefin or paraffin. This so called "back end" approach requires a separate hydrotreating system for each carbon number fraction as well as the addition of a requisite amount of hydrogen to each system. An alternative method is to hydrotreat the feed stream before separation using the contained hydrogen as the source of hydrogen for the conversion. This so-called "front end" approach has the advantage of removing a significant portion of the hydrogen from the feed stream to the cold box thereby reducing the size and refrigeration requirements of the cold box.

U.S. Patent Publication 2003-0233017-A1 (Dec. 18, 2003) discloses a method to maintain mixed phase flow and temperature control through the downflow boiling point reactor by removing a relative large liquid stream enriched in $C_6$+ components from a $C_5$/$C_6$ splitter and feeding it to the reactor together with the net vapor feed and reactor liquid recycle stream whereby the $C_6$+ components are returned to the splitter in the vapor fraction from the reactor vapor/liquid separation drum.

It is an advantage of the present invention that the withdrawal and return of the $C_6$+ components from the $C_5$/$C_6$ splitter is eliminated. It is a further advantage that a smaller $C_5$/$C_6$ splitter and associated reboilers and condensers are required.

SUMMARY OF THE INVENTION

The present invention provides an improved "front end" hydrotreating system that allows for effective control of the temperature within a bed of catalyst which is selectively hydrogenating acetylenes and dienes in a stream containing hydrogen, methane, $C_2$-$C_6$ olefins and paraffins, $C_2$-$C_6$ acetylenes and dienes, benzene, toluene, xylenes, and other $C_6$+ components. The invention utilizes a downflow boiling point reactor wherein the heat of reaction is absorbed by the liquid in the reactor which produces a vapor. Besides the feed to the reactor, there is a recirculating stream from a first downstream liquid/vapor separator which is fed at a rate sufficient to ensure that the catalyst particles within the reactor are wetted.

A third liquid stream, which is recycled to the reactor is provided by partially condensing an amount of the vapor from the first downstream liquid/vapor separator corresponding to the mass evaporated in the reactor, which is usually and preferably in the range of about 30 to 50% of the vapor flow from the first downstream liquid/vapor separator, and passing the partially condensed stream to a second downstream liquid/vapor separator. The composition of the third stream controls the steady state composition of the liquid flowing through the reactor. The steady state composition of the material flowing through the reactor along with the pressure determines the reactor temperature profile.

In a "boiling point reactor" a liquid phase is always maintained, even if the reaction components would be vaporized by the exothermic heat of reaction. In any reaction where the reaction stream is likely to be vaporized, an inert higher boiling component may be added to maintain a liquid phase.

BRIEF DESCRIPTION OF THE DRAWING

The FIGURE is a flow diagram in schematic form of one embodiment of the invention.

DETAILED DESCRIPTION OF THE PREFERRED EMBODIMENT

Catalysts which are useful include the Group VIII metals. The catalyst may be used as individual Group VIII metal components or in admixture with each other or modifiers as known in the art, particularly those in Group VIB and IB. Catalysts which are useful for the selective hydrogenation of acetylenes and dienes include palladium oxide supported on alumina. Nickel catalyst also catalyzes the selective hydrogenation of the 1,2-butadiene and acetylenes. However, the palladium catalyst is preferred for these reactions. One such catalyst contains 0.34 wt. % palladium supported on ⅛ inch spheres designated G68C and supplied by Süd-Chemie (formerly United Catalyst Inc.). Another catalyst comprises 0.5 wt. % palladium supported on 8-12 mesh spheres and designated E144SDU as supplied by Calcicat, Catalyst and Performance Chemicals Division, Mallinckrodt, Inc. For best results the catalyst is supported in structured packing as disclosed in commonly owned U.S. Pat. No. 5,730,843. The catalyst may, however, be simply loaded into the reactor.

Referring now to the FIGURE, selective hydrogenation of acetylenes and diolefins in a hydrocarbon stream containing significantly larger amounts (molar basis) of hydrogen and olefins than the acetylenes and diolefins is carried out in a downflow boiling point reactor. The downflow boiling point reactor, shown as column 10 is a vertically disposed reactor containing the particulate catalyst supported in a structured packing at 12. The gaseous feed stream is fed via flow line 101 to the top of the column 10. Also fed to flow line 101 is liquid in flow line 102 derived from separator 20 and flow line 104 which is derived from liquid/vapor separator 30 as more particularly described below. Gas and liquid streams flow concurrently downward through the column with the flow regime being gas continuous. The concurrent flow of gas and liquid eliminates the possibility of a runaway reaction. A trim heater (not shown) may be installed in line 101 to ensure that the inlet feed temperature to the reactor is sufficient to initiate the selective hydrogenation reactions.

The reactor 10 is operated adiabatically so that the heat of reaction is accounted for by preferentially evaporating the lighter liquid phase components. Effluent from the reactor in flow line 105 is fed to vapor/liquid separator 20 where the vapor and liquid are separated. The vapor in flow line 106 passes to condenser 70 which is operated to condense sufficient of the vapor to make up the mass evaporated in the reactor 10 and the liquid recovered in flow line 104 from separator 30. Liquid in flow line 102 is fed back to reactor 10. The flow rate of the stream in flow line 102 is a variable and is maintained at least sufficient to ensure that the catalyst particles are fully wetted at all positions in the reactor 10. The stream in flow line 104 provides makeup mass corresponding to the mass evaporated in the reactor that leaves the reactor system as part of the stream in flow line 103. The composition of the stream in flow line 104 controls the steady state composition of liquid flowing through the reactor 10. This is an important operating parameter which in combination with the reactor pressure determines the reactor temperature profile. A slip stream is taken by flow line 107 to control the liquid inventory in the vapor/liquid separator vessel 20.

Column 40 is a $C_5/C_6$ splitter. Feed to the column is the vapor from the separator 30 in flow line 103. The column 40 is designed to recover a vapor distillate fraction via flow line 108 which is essentially free of $C_6+$ components and a bottoms liquid product in flow line 109 which is essentially free of $C_5$ and lighter components. The overheads are taken via flow line 130 and passed through partial condenser 50 where the heavier components are condensed. The overheads are collected in receiver separator 60 where liquid hydrocarbon is withdrawn via flow line 120 and returned to the column 40 as reflux. Water is taken out via flow line 110. As noted distillate product is removed via flow line 108.

EXAMPLE

Feed to the system depicted in FIGURE is the vapor product from the quench tower of an olefins producing steam cracker after compression and acid gas ($CO_2$ and $H_2S$) removal. The reactor is loaded with approximately 14,000 ft$^3$ structured packing loaded with hydrogenation catalyst. Bed dimensions are approximately 15 ft diameter by 70 ft long. Operating conditions for the reactor are: reactor top/bottom pressure 250/240 psia; liquid recycle rate (stream in flow line 102) 4,792,100 lbs./hr.; slip stream in flow line 107, 2854 lbs./hr. The distillation column 40 is a column configured with a 16.4 ft diameter 20 stage (theoretical) top section and 10.5 ft 20 stage (theoretical) bottom section. Design conditions for the distillation column 40 are: reflux ratio 0.18; reflux temperature 136° F., condenser pressure is 238 psia; column pressure drop is 2 psi. Heat and material balance results are given in the TABLE.

TABLE

HEAT AND MATERIAL BALANCE

|  | 101 | 102 | 103 | 104 | 105 |
|---|---|---|---|---|---|
| Temperature ° F. | 205.3 | 223.5 | 122.8 | 23.4 | 223.4 |
| Pressure psi | 250 | 240 | 240 | 240 | 240 |
| Vapor Frac | 0 | 0 | 1 | 0 | 0 |
| Mole Flow lbmol/hr | 102,509 | 64,306 | 28,127 | 8,4156 | 100,895 |
| Mass Flow lb/hr | 6,113,970 | 4,792,100 | 786,912 | 527,105 | 6,108,390 |
| Volume Flow cuft/hr | 1,030,270 | 115,181 | 670,898 | 12,946 | 1,133,170 |
| Enthalpy MMBtu/hr | −468.695 | −354.083 | −123.249 | −131.631 | −470.611 |
| Mass Flow lb/hr |  |  |  |  |  |
| H2 | 9,409 | 130 | 6,123 | 19 | 6,271 |
| CO | 1,617 | 65 | 1,541 | 12 | 1,617 |
| CO2 | 0.0 | 0.0 | 0.0 | 0.0 | 0.0 |
| H2S | 0.0 | 0.0 | 0.0 | 0.0 | 0.0 |
| METHANE | 130,940 | 10,340 | 118,388 | 2,195 | 130,924 |
| ACETYLENE | 4,589 | 258 | 846 | 72 | 1,178 |
| ETHYLENE | 314,462 | 57,820 | 243,092 | 14,926 | 315,852 |
| ETHANE | 74,413 | 17,235 | 54,817 | 4,696 | 76,755 |
| METHYLACETYL | 5,990 | 703 | 526 | 212 | 1,446 |
| PROPADIENE | 9,659 | 3,512 | 3,022 | 1,010 | 7,560 |
| PROPYLENE | 288,274 | 114,196 | 144,919 | 33,866 | 293,186 |
| PROPANE | 10,527 | 5,048 | 6,157 | 1,513 | 12,727 |
| BUTADIENE | 43,692 | 3,347 | 1,334 | 926 | 5,603 |
| T-BUTENE | 69,576 | 42,798 | 15,005 | 11,701 | 69,273 |
| 1-BUTENE | 176,079 | 125,474 | 54,133 | 35,159 | 214,566 |
| CIS2BUTE | 74,823 | 47,384 | 14,824 | 12,536 | 74,474 |
| ISOBUTENE | 60,114 | 34,811 | 15,422 | 9,824 | 60,024 |
| ISOBUTANE | 22,351 | 12,306 | 6,464 | 3,561 | 22,360 |
| BUTANE | 29,539 | 18,297 | 6,868 | 4,969 | 30,040 |
| 1PENTENE | 456,502 | 346,437 | 41,364 | 73,611 | 462,722 |
| HEXANE | 419,239 | 363,810 | 8,944 | 45,915 | 418,925 |
| OCTANE | 330,971 | 318,500 | 406 | 11,478 | 330,339 |
| BENZENE | 1,910,170 | 1,728,940 | 21,501 | 156,906 | 1,907,720 |
| TOLUENE | 1,293,470 | 1,235,340 | 2,574 | 53,510 | 1,291,380 |
| M-XYLENE | 7,223 | 7,052 | 3 | 153 | 7,207 |
| O-XYLENE | 5,416 | 5,302 | 2 | 102 | 5,406 |
| P-XYLENE | 7,937 | 7,745 | 4 | 171 | 7,920 |
| ETHYLBENZENE | 10,438 | 10,170 | 6 | 240 | 10,416 |
| STYRENE | 4,429 | 4,338 | 2 | 82 | 4,421 |
| NONANE | 3 | 3 | 0 | 0 | 3 |
| DECANE | 3 | 3 | 0 | 0 | 3 |
| UNDECANE | 1 | 1 | 0 | 0 | 1 |
| DODECANE | 0 | 0 | 0 | 0 | 0 |
| TRIDECANE | 0 | 0 | 0 | 0 | 0 |
| TETRADECANE | 0 | 0 | 0 | 0 | 0 |

TABLE-continued

HEAT AND MATERIAL BALANCE

| | | | | | |
|---|---|---|---|---|---|
| PENTADECANE | 0 | 0 | 0 | 0 | 0 |
| WATER | 53,958 | 39,749 | 4,455 | 9,703 | 54,278 |
| PROPADIENE | 7,964 | 3 | 0 | 1 | 4 |
| ISOPRENE | 8,085 | 652 | 63 | 123 | 838 |
| HEXADIENE | 3,897 | 23 | 1 | 3 | 26 |
| HEXENE | 149,072 | 131,692 | 3,769 | 17,380 | 152,927 |
| PENTANE | 119,144 | 98,612 | 10,340 | 20,532 | 130,003 |

| | 106 | 107 | 108 | 109 | 110 |
|---|---|---|---|---|---|
| Temperature ° F. | 223.5 | 224.7 | 80.6 | 397.9 | 80.6 |
| Pressure psi | 240 | 240 | 238 | 240 | 238 |
| Vapor Frac | 1 | 0 | 1 | 0 | 0 |
| Mole Flow lbmol/hr | 36,588 | 104 | 27,527 | 523 | 57 |
| Mass Flow lb/hr | 1,316,290 | 7,854 | 748,504 | 43,000 | 1,026 |
| Volume Flow cuft/hr | 1,019,730 | 189 | 604,109 | 1,210 | 17 |
| Enthalpy MMBtu/hr | −116.524 | −0.532 | −121.285 | −2.573 | −6.991 |

Mass Flow lb/hr

| | | | | | |
|---|---|---|---|---|---|
| H2 | 6,141 | 0 | 6,123 | 0.0 | 0.0 |
| CO | 1,552 | 0 | 1,541 | 0.0 | 0.0 |
| CO2 | 0.0 | 0.0 | 0.0 | 0.0 | 0.0 |
| H2S | 0.0 | 0.0 | 0.0 | 0.0 | 0.0 |
| METHANE | 120,584 | 17 | 118,405 | 0.0 | 0.0 |
| ACETYLENE | 919 | 0 | 847 | 0.0 | 0.0 |
| ETHYLENE | 258,032 | 94 | 243,187 | 0.0 | 0.0 |
| ETHANE | 59,520 | 28 | 54,845 | 0.0 | 0.0 |
| METHYLACETYL | 743 | 1 | 527 | 0.0 | 0.0 |
| PROPADIENE | 4,047 | 6 | 3,028 | 0.0 | 0.0 |
| PROPYLENE | 178,990 | 186 | 145,104 | 0.0 | 0.0 |
| PROPANE | 7,679 | 8 | 6,165 | 0.0 | 0.0 |
| BUTADIENE | 2,256 | 6 | 1,340 | 0.0 | 0.0 |
| T-BUTENE | 26,474 | 71 | 15,076 | 0.0 | 0.0 |
| 1-BUTENE | 89,092 | 206 | 54,338 | 0.0 | 0.0 |
| CIS2BUTE | 27,090 | 79 | 14,903 | 0.0 | 0.0 |
| ISOBUTENE | 25,213 | 57 | 15,479 | 0.0 | 0.0 |
| ISOBUTANE | 10,054 | 20 | 6,484 | 0.0 | 0.0 |
| BUTANE | 11,744 | 30 | 6,898 | 0.0 | 0.0 |
| 1PENTENE | 116,285 | 551 | 41,747 | 168 | 0.0 |
| HEXANE | 55,115 | 584 | 339 | 9,189 | 0.0 |
| OCTANE | 11,839 | 594 | 0.0 | 1,000 | 0.0 |
| BENZENE | 178,773 | 2,776 | 336 | 23,941 | 0.0 |
| TOLUENE | 56,040 | 2,056 | 0 | 4,630 | 0.0 |
| M-XYLENE | 155 | 14 | 0.0 | 18 | 0.0 |
| O-XYLENE | 104 | 10 | 0.0 | 12 | 0.0 |
| P-XYLENE | 175 | 16 | 0.0 | 20 | 0.0 |
| ETHYLBENZENE | 245 | 20 | 0.0 | 26 | 0.0 |
| STYRENE | 83 | 8 | 0.0 | 10 | 0.0 |
| NONANE | 0 | 0 | 0 | 0 | 0 |
| DECANE | 0 | 0 | 0 | 0 | 0 |
| UNDECANE | 0 | 0 | 0 | 0 | 0 |
| DODECANE | 0 | 0 | 0 | 0 | 0 |
| TRIDECANE | 0 | 0 | 0 | 0 | 0 |
| TETRADECANE | 0 | 0 | 0 | 0 | 0 |
| PENTADECANE | 0 | 0 | 0 | 0 | 0 |
| WATER | 14,529 | 50 | 1,242 | 0.0 | 1,026 |
| PROPADIENE | 1 | 0 | 0 | 0.0 | 0.0 |
| ISOPRENE | 186 | 1 | 56 | 8 | 0.0 |
| HEXADIENE | 3 | 0.0 | 0.0 | 1 | 0.0 |
| HEXENE | 21,235 | 212 | 303 | 3,678 | 0.0 |
| PENTANE | 31,391 | 154 | 10,193 | 301 | 0.0 |

The invention claimed is:

1. A process for the hydrogenation of acetylenes and dienes in a stream containing hydrogen, methane, $C_2$-$C_6$ olefins and paraffans, $C_2$-$C_6$ acetylenes, dienes, benzene, toluene, xylenes, and other $C_{6+}$ components comprising the steps of:

(a) passing said stream over a hydrogenation catalyst contained in a downflow boiling point reactor operated at the boiling point of the mixture in the reactor and the heat of reaction is absorbed by the boiling liquid to produce a first liquid/vapor effluent and a portion of the acetylenes and dienes are converted to their corresponding olefins and paraffins of the same carbon number;

(b) separating the first liquid/vapor effluent to a first liquid and first vapor;

(c) returning a portion of the first liquid to said downflow boiling point reactor in an amount to ensure that the catalyst is fully wetted at all positions within said downflow boiling point reactor;

(d) condensing a portion of the first vapor corresponding to the mass evaporated in the reactor to produce a second liquid/vapor effluent;

(e) separating the second liquid/vapor effluent to a second liquid and second vapor;
(f) returning said second liquid to said downflow boiling point reactor, thereby controlling the steady state composition of the material flowing through the reactor; and
(g) feeding said second vapor to a $C_5/C_6$ splitter where $C_5$ and lighter material are taken as overheads and $C_6$ and heavier material are taken as bottoms.

2. The process according to claim 1 wherein the first liquid and said second liquid are recycled back to the top of said downflow boiling point reactor.

3. The process according to claim 1 wherein the portion of the first vapor condensed is in the range of about 30 to 50% of the vapor.

* * * * *

UNITED STATES PATENT AND TRADEMARK OFFICE
CERTIFICATE OF CORRECTION

PATENT NO. : 7,408,090 B2
APPLICATION NO. : 11/101098
DATED : August 5, 2008
INVENTOR(S) : Lawrence A. Smith, Jr. et al.

It is certified that error appears in the above-identified patent and that said Letters Patent is hereby corrected as shown below:

In Claim 1, column 5, line 60, the word "paraffans" should be --paraffins--.

Signed and Sealed this

Twenty-eighth Day of October, 2008

JON W. DUDAS
*Director of the United States Patent and Trademark Office*